United States Patent [19]

Hansen et al.

[11] Patent Number: 5,349,085
[45] Date of Patent: Sep. 20, 1994

[54] X-RAY CONTRAST AGENTS

[75] Inventors: Per-Egil Hansen, Dalbo; Hugo Holtermann, Hovik, Baerum; Knut Wille, Osterås, all of Norway

[73] Assignee: Nycomed Imaging AS, Oslo, Norway

[21] Appl. No.: 960,231

[22] Filed: Oct. 13, 1992

Related U.S. Application Data

[63] Continuation of Ser. No. 800,980, Dec. 2, 1991, abandoned, which is a continuation of Ser. No. 568,727, Aug. 17, 1990, abandoned, which is a continuation of Ser. No. 924,925, Oct. 30, 1986, abandoned, which is a continuation of Ser. No. 549,463, Nov. 7, 1983, abandoned.

[30] Foreign Application Priority Data

Nov. 8, 1982 [GB] United Kingdom ............... 8231796

[51] Int. Cl.$^5$ ............................................. C07C 233/64
[52] U.S. Cl. ................................................. 564/153; 424/5
[58] Field of Search ................................. 564/153; 424/5

[56] References Cited

U.S. PATENT DOCUMENTS

| | | | |
|---|---|---|---|
| 3,632,738 | 1/1972 | Ingelman | 424/5 |
| 3,678,152 | 7/1972 | Bjork et al. | 424/5 |
| 3,692,824 | 9/1972 | Bjork et al. | 424/5 |
| 3,701,771 | 10/1972 | Almen et al. | 424/5 |
| 3,763,226 | 10/1973 | Ingelman | 424/5 |
| 3,763,227 | 10/1973 | Ingelman | 424/5 |
| 3,772,376 | 11/1973 | Ehstrand et al. | 424/5 |
| 3,804,892 | 4/1974 | Ingelman | 424/5 |
| 3,939,204 | 2/1976 | Buttermann | 424/5 |
| 4,239,747 | 12/1980 | Pfeiffer et al. | 424/5 |
| 4,250,113 | 2/1981 | Nordal et al. | 564/153 |
| 4,348,377 | 9/1982 | Felder et al. | 424/5 |
| 4,426,371 | 1/1984 | Pfeiffer et al. | 424/5 |
| 4,474,747 | 10/1984 | Dimo et al. | 424/5 |

Primary Examiner—Shailendra Kumar
Attorney, Agent, or Firm—Bacon & Thomas

[57] ABSTRACT

Compounds of the general formula:

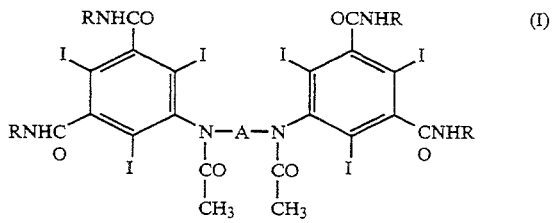

(where R is a group —CH(CH$_2$OH)$_2$ or —CH$_2$CH(OH)CH$_2$OH and A is a group —CH$_2$CH(OH)CH$_2$— or —CH$_2$CH(OH)CH(OH)CH$_2$—) possess a package of favourable parameters which render them of particular use not only in all forms of intravascular visualisation but also in myelography.

The compounds are prepared by reaction of an appropriate 5-acetylamino-N,N'-bis(hydroxypropyl)-2,4,6-triiodoisophthalamide with an agent effective to introduce the appropriate hydroxyalkylene group such as for example epichlorohydrin or 1,4-dichloro-2,3-dihydroxybutane.

1 Claim, No Drawings

X-RAY CONTRAST AGENTS

This application is a continuation of application Ser. No. 07/800,980, filed Dec. 2, 1991, now abandoned, which is a continuation of application Ser. No. 07/568,727, filed Aug. 17, 1990, now abandoned, which is a continuation of application Ser. No. 06/924,925, filed Oct. 30, 1986, now abandoned, which is a continuation of application Ser. No. 06/549,463, filed Nov. 7, 1983, now abandoned.

The present invention relates to novel nonionic X-ray contrast agents, to compositions containing them and to methods for their manufacture.

In our British Patent Specification No. 1,321,591 we describe and claim certain non-ionic compounds as X-ray contrast agents, such compounds representing an important advance over previously known ionic X-ray contrast agents in respect of side effects due to high concentrations of ions and/or to high osmolality. Such compounds are suitable for one or more possible fields of X-ray visualisation but are not usually suitable for a wide range or spectrum of such uses. In general, non-ionic X-ray contrast agents may be of use in two main fields, namely:

Intravascular visualisation, including urography and angiography, for example cerebral, coronary and peripheral angiography, and Myelography, i.e. injection into the cerebrospinal fluid.

Radiologists have used different X-ray contrast agents particularly adapted to different fields of use but there are clearly advantages if it is possible to use a single X-ray contrast agent for a wide range of uses; apart from economies of scale in manufacture, it is also more satisfactory for the radiologist to be able to use experience of a contrast agent gained in one field of use, e.g. urography, in some other field, e.g. angiography or myelography. For the purposes of this specification an X-ray contrast agent which can be used in all forms of intravascular visualisation and myelography is termed a 'general X-ray contrast agent'.

A general X-ray contrast agent should possess a 'package' of favourable parameters, namely low toxicity, low osmolality, low viscosity, low nephrotoxicity, high urinary excretion and, in particular, the ability to produce solutions of high concentration but low osmolality.

It is known that X-ray contrast agents which possess close structural similarities may nevertheless possess very different properties such as for example toxicity. Thus it is a difficult empirical task to identify a compound which possesses a complete package of favourable parameters and which can be used as a general X-ray contrast agent.

As indicated above, one of the principal advantages of non-ionic X-ray contrast agents is their low osmolality as compared with ionic compounds, due to the reduction in the number of dissolved particles present at a particular iodine concentration. Low osmolality is desirable in order to reduce tissue damage arising from unduly high osmotic pressures generated by the very high concentrations at which X-ray contrast agents are administered. The osmolality can be reduced still further if the number of iodine atoms in each non-ionic molecule can be increased and it has been proposed to use relatively large molecules containing two triiodophenyl rings joined by a short chain. However, such large molecules commonly exhibit nephrotoxicity and are thus thought to be unsuitable for vascular X-ray visualisation.

In particular, European Patent Application 0023992A1 of Bracco Industria Chemica S.p.A. describes non-ionic X-ray contrast agents of the general formula

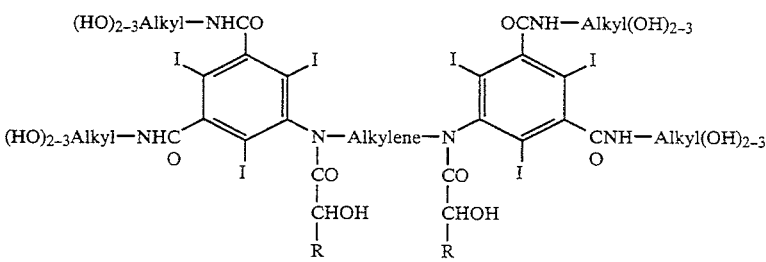

where $(HO)_{2-3}$ Alkyl represents a 1,3-dihydroxyisopropyl, 2,3-dihydroxypropyl or 1,3-dihydroxy-2-hydroxymethylisopropyl group, R represents hydrogen or methyl and Alkylene represents a divalent alkylene group with 2 to 10 carbon atoms, which can be substituted by hydroxy functions, or a mono-, di- or poly-oxaalkylene group with 4 to 12 carbon atoms, which can be substituted by hydroxy functions. These compounds are indicated only for visualisation of the subarachnoid space, where the question of nephrotoxicity is not particularly relevant. Although the Alkylene group is permitted to carry hydroxy functions, the only compounds for which any results are given do not have hydroxy functions on the group Alkylene. Indeed in our hands the Bracco synthesis as applied to the preparation of such compounds having hydroxy alkylene chains, invariably produced rearranged derivatives.

It should be noted that the Bracco compounds all carry a relatively large number of hydroxyl groups including one in each of the acyl (lactyl) functions. This would be expected to lead to relatively high viscosities and it would normally be thought desirable to avoid additional hydroxyl functions, for example, on the Alkylene group, in the absence of other compensating factors. Furthermore, it is well known that a hydroxyl group on an N-alkyl grouping of a triiodoaniline often undergoes nucleophilic reaction at high temperatures at the adjacent C-I bond with cyclisation. The Bracco patent suggests protection of such OH groups but this would clearly complicate any synthesis and would lead a chemist to choose the simpler solution of avoiding hydroxyl groups in Alkylene.

We have now found that a small group of nonionic X-ray contrast agents of the same general type as those of European Patent Application 0023992A1 but possessing acetyl groups in place of the two lactyl groups and having a hydroxylated alkylene chain joining the two triiodoaniline rings, have outstanding properties, including low nephrotoxicity, which enable them to be used for vascular as well as for subarachnoid visualisation, that is as general X-ray contrast agents.

According to the present invention, therefore, we provide compounds of the general formula I

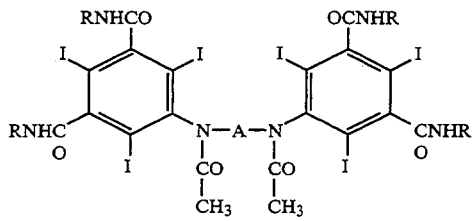

(where R is a group —CH(CH₂OH)₂ or —CH₂CH(OH)CH₂OH and A is a group —CH₂CH(OH)CH₂— or —CH₂CH(OH)CH(OH)CH₂—) including the stereoisomeric forms thereof separately or in combination.

Formula I includes four compounds, namely Compound A;   R=—CH₂CH(OH)CH₂OH;   A=—CH₂CH(OH)CH₂—
Compound B;   R=—CH(CH₂OH)₂;   A=—CH₂CH(OH)CH₂—
Compound C;   R=—CH₂CH(OH)CH₂OH; A=—CH₂CH(OH)CH(OH)CH₂—
Compound D;   R=—CH(CH₂OH)₂;   A=—CH₂CH(OH)CH(OH)CH₂—

These compounds may exist in several isomers due to chiral carbon atoms. In addition, the compounds exhibit exo/endo isomerism due to restricted rotation of the N-CO bond in the acetamido groups caused by the proximity of the bulky iodine atoms. The invention extends to all the isomeric forms of the compounds, including optically active, racemic and meso isomers.

As indicated above, the compounds of the invention exhibit a package of outstanding properties rendering them capable of use in all forms of X-ray visualisation. The compounds possess osmolalities significantly lower, for example more than 50% lower, than comparable compounds having a single triiodinated benzene ring. Thus, the osmolality of Compound A is 196 mOs/Kg H₂O at 300 mgI/ml and 233 mOs/Kg H₂O at 350 mgI/ml. The osmolality of Compound B is 120 mOs/Kg H₂O at 195 mgI/ml and 160 mOs/Kg H₂O at 295 mgI/ml. The osmolality of Compound C is 242 mOs/Kg H₂O at 370 mgI/ml. The osmolality of Compound D is 189 mOs/Kg H₂O at 300 mgI/ml and 224 mOs/Kg H₂O at 350 mgI/ml. It will be noted from the above values that the compounds are capable of forming solutions of very high concentration.

The nephrotoxicity levels of the compounds are acceptably low, compared to many known 'bis' X-ray contrast agents. The nephrotoxicity of Compound A in rabbits is >7.5 gI/Kg, that of Compound B is also >7.5 gI/Kg and that of Compound C is >10.5 gI/Kg. The intravenous toxicities of the compounds in mice are also low, that of Compound A being 14.4 gI/Kg, that of Compound B and Compound C being 18.5 gI/Kg.

The viscosities of the compounds at high concentrations are acceptable, given their high molecular weights and content of hydroxyl groups. Thus, the specific viscosity of Compound A at 300 mgI/ml is 18.9 cP at 20° C. and 8.7 cP at 37° C., while at 350 mgI/ml it is 44.5 cP at 20° C. and 17.7 cP at 37° C. The viscosity of Compound B at 300 mgI/ml is 18.4 cP at 20° C. and 8.7 cP at 37° C., while at 370 mgI/ml it is 62 cP at 20° C. and 23.6 cP at 37° C. The viscosity of Compound C at 300 mgI/ml is 22.7 cP at 20° C. and 10.3 cP at 37° C., while at 350 mgI/ml it is 54.7 cP at 20° C. and 21.7 cP at 37° C.

The urinary excretion levels of the compounds of the invention in rabbits are higher than those expected for the X-ray contrast agents presently in clinical use. Such agents are generally excreted in the range 50–150 mg I/ml urine when the compound is given at a dose of 500 mgI/kg body weight. In comparison, compounds of the present invention when given at a dose of only 200 mg I/kg are excreted as listed below. The figures are median values and the figures in brackets are the number of animals investigated.

| Compound A | 218 mg I/ml | (9) |
| Compound B | 218 mg I/ml | (7) |
| Compound C | 230 mg I/ml | (10) |
| Compound D | 191 mg I/ml | (9) |

The subarachnoid tolerances of the compounds A and C in unanaesthetised rabbits were particularly good being generally at least as good as that of N,N-bis (2,3-dihydroxypropyl)-5-[N-(2,3-dihydroxypropyl)acetamido]-2,4,6-triiodoisophthalamide. In anaesthetised rats no motoric or convulsive effects were observed on administration of Compounds A and C to 7 out of 8 rats.

The present invention also provides radiological compositions comprising as active ingredient at least one of the compounds of formula I as hereinbefore defined in association with a radiological carrier.

The radiological compositions of the present invention are conveniently presented in a form suitable for administration by injection, for example, in ampoules or vials. The capacity of the ampoule or vial may be, for example, from 5 to 500 ml and the concentration may, for example, be from 20 to 500 mg I/ml.

The compounds of the present invention may be prepared in any convenient manner, but the following process is of particular interest and constitutes a further feature of the present invention.

Thus there is provided a process for the preparation of the compounds of formula I as hereinbefore defined which comprises reacting the compound of formula:

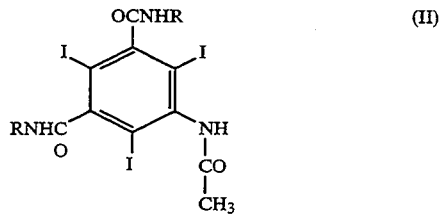

(where R has the above meaning) or a hydroxyl protected derivative thereof with a compound of the formula III X-A-X' (where X and X' are readily eliminatable atoms or groups and A has the above meaning) or a hydroxyl protected derivative thereof or a corresponding epoxide in which one or both of the substituents X and X' and the hydroxyl group on an adjacent carbon atom are replaced by -O- followed, where required, by removal of any unwanted protecting groups. Thus, the groups X and X' compounds of Formula III may be chosen from halogen atoms, e.g. chlorine, bromine or iodine, or sulphate or hydrocarbylsulphonyloxy groups, e.g. alkyl- or aryl-sulphonyloxy groups such as tosyloxy or mesyloxy. The compound of Formula III may thus be epichlorohydrin or 1,4-dichloro-2,3-dihydroxybutane.

As indicated above, the hydroxyl groups present in the groups R and A may, if desired, be in a hydroxyl protected form; suitable protecting groups include acyl groups such as acetyl or, where adjacent hydroxyl groups are concerned, cyclic ketal or acetal groups.

The reaction between compounds II and III is preferably effected in the presence of an acid binding agent, for example an organic or inorganic base preferably in an aqueous or alcoholic medium such as water or an alkanol or glycol; an alkali metal alkoxide such as sodium methoxide or an alkali metal hydroxide such as sodium or potassium hydroxide may be used as base.

Any protecting groups may be removed by standard methods, for example hydrolysis. The compound of formula II may be prepared by acetylation of the corresponding compound having a free amino group and in such a reaction, hydroxyl groups in the substituents R may also be acetylated. Such acetyl groups may be removed by basic hydrolysis.

If necessary, the product may be purified by preparative chromatography.

The compounds of formula II may be prepared in any convenient manner, for example, by reaction of 5-acetamido-2,4,6-triiodoisophthaloyl chloride and/or 5-diacetylamino-2,4,6-triiodoisophthaloyl chlorine with 1,3-dihydroxy-2-propylamine or 2,3-dihydroxypropylamine followed, where the 5-diacetylamino compound is used, by removal of one N-acetyl group, e.g. by alkaline hydrolysis at slightly elevated temperature. The reaction may, for example, be effected in the presence of dimethylformamide or dioxan as solvent, conveniently in the additional presence of an alkali metal or alkaline earth metal carbonate or bicarbonate such as potassium bicarbonate.

A compound of formula II may also be prepared for example, by acetylation of a compound of the formula:

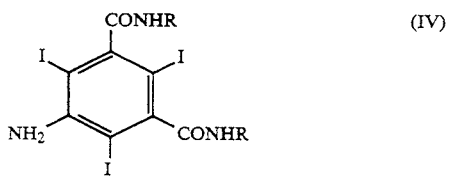

(where R has the above meanings). Acetylation may be effected by any convenient method e.g. by the use of acetic anhydride (which can also serve as the solvent) together with catalytic amounts of a mineral acid e.g. sulphuric or perchloric acid, or by the use of an acid halide preferably in a polar solvent such as dimethylformamide or dimethylacetamide. Where unwanted O-acetyl groupings are formed these may be removed either at this stage or after the reaction with the compound of formula III. The basic hydrolysis of the O-acetyl grouping may for example, be effected using aqueous alkali metal hydroxide, e.g. sodium hydroxide, the reaction preferably being carried out at slightly elevated temperature, e.g. about 50° C.

In addition, depending on the acylating agent used, other products may be formed and require separation. When an acyl anhydride such as acetic anhydride is used with concentrated sulphuric acid as catalyst, the primary amino group is often, in part, bis-acetylated, such that an overacetylated product is obtained. In general a mixture of acetylated products will be obtained. If desired, the bisacetylamino group may be hydrolysed to the monoacetylamino group under mild basic conditions e.g. by the use of sodium hydroxide in, for example, methanol prior to N-hydroxyalkylation. It is, however, possible to effect N-hydroxyalkylation using the bis-acetylamino compound with simultaneous solvolysis.

The following examples are given by way of illustration only: all temperatures are in °C:

EXAMPLE 1

1,4-Bis(acetylamino)-N,N'-bis[3,5-bis(2,3-dihydroxypropylaminocarbonyl)-2,4,6-triiodophenyl]-2,3-dihydroxybutane (Compound C)

5-Acetylamino-N,N'-bis(2,3-dihydroxypropyl)-2,4,6-triiodoisophthalamide (75 g, 100.4 mmol) was dissolved in methanol (230 ml) containing sodium hydroxide (6.03 g, 150 mmol) at room temperature. To this solution 1,4-dichloro-2,3-dihydroxy-butane, dissolved in methanol (25 ml), was added and the resulting mixture was stirred at room temperature for 42 hours. The above described 1,4-dichloro-2,3-dihydroxybutane was prepared as follows; 1,2,3,4-diepoxybutane (4.89 g, 56.9 mmol) was dissolved in water (70 ml) and concentrated hydrochloric acid (9.5 ml) was slowly added while the reaction-mixture was cooled in ice-water. After stirring for 30 min. the reaction-mixture was concentrated, and redissolved in methanol (25 ml).

The reaction was quenched by adding concentrated aqueous hydrochloric acid (pH 2). Filtration and evaporation gave the crude reaction product (85.0 g). This material was purified using preparative LC (Waters LC 500, prepPak C-18). Eluent: 14% methanol in water. 8 runs of 8.5 g. The product was eluted between 3.0 1 and 4.5 1, and the total eluent was about 9 1. The purest fractions were collected and evaporated to dryness at 60° C. in vacuo. Yield: 24 g, melting point 228°-233° C. HPLC: RP-18. 5 μm, gradient 5–17% acetonitrile. 3 peaks. 18,47 min (4.6%). 19,20 min (61.5%). 20,85 min (33.5%). These three peaks correspond to endo/endo, exo/exo and exo/endo (endo/exo).

The product gave three spots on TLC (precoated TLC plates. Silica gel 60 F-254 from Merck AG) Eluent: n-BuOH: H$_2$O: HOAc. (50:25:11), R$_f$ 0.19, 0.18 and 0.15.

Found C: 27.64, H:2.94, I: 48.3 Calc. for C$_{36}$H$_{46}$I$_6$N$_6$O$_{16}$ C: 27.36, H: 2.93, I: 48.2.

EXAMPLE 2

1,3-Bis(acetylamino)-N,N'-bis[3,5-bis(1,3-dihydroxy-2-propylaminocarbonyl)-2,4,6-triiodophenyl]-2-hydroxypropane (Compound B)

5-Acetylamino-N,N'-bis(1,3-dihydroxy-2-propyl)-2,4,6-triiodoisophthalamide (400 g, 0.535 mol) was slurried in water (1600 ml) at room temperature. Sodium hydroxide (16.1 g, 0.040 mol) was added followed by epichlorohydrin (37.2 g, 0.40 mol). After about 3 days the starting material was completely dissolved. HPLC (Column: Brownlee Labs, RP 18 Spheri 5 5 um, 4.6 mm i.d.×25 cm. Linear gradient: 1–20% CH$_3$CN in water, 0.2% per min, flow: 1 ml per min. Detector: UV 254 nm) of the reaction mixture showed about 60% of the "dimer" compound, about 23% of the "monomer"

compound and about 2% of the starting material. The rest of the peaks represented unidentified compounds. The solution was neutralized with hydrochloric acid and evaporated to dryness at 60° in vacuo. The product was dissolved in a mixture of 17% methanol in water to a final volume of 600 ml and purified by preparative liquid chromatography (Instrument: Prep LC/System 500 (Waters Ass). Column: PrepPak-500/$C_{18}$. Eluent: 17% methanol in water. Flow: about 200 ml/min). The purification was performed by injecting a portion (15 ml) of the solution mentioned above. The "monomeric" compound was eluted first and was readily separated from the desired product which followed. Other impurities were eluted from the column after the desired product. When a sufficient volume of the eluent had been passed through the column to remove the most strongly retained components, the procedure was repeated with a new portion of the crude product. The purest fractions of the product were eluted between 1.5–4.5 l and total volume of eluent used for one injection was about 8 l. The corresponding fractions were collected and evaporated to dryness at 50°–60° in vacuo.

The purest fractions were purified once more by preparative LC. This time the column was loaded with 5 g substance (10 ml solution) and eluted with 14% methanol in water. The product was eluted between 2.4–5.0 l, and the total eluent was about 8 l. The purest fractions were collected and evaporated to dryness at 50°–60° in vacuo. Yield: 70 g, Melting point: 305°–310° decomp. HPLC (the same conditions as described above) show two peaks with retention times 39.97 and 44.04 minutes.

Probably these two peaks represented the endo/exo and exo/exo isomers. The product gave three spots by TLC (precoated TLC Plates Silica Gel 60 F-254 gtp, Merck A. G. and developed in n-BuOH: HOAC:-$H_2O$=50:11:25) with $R_f$ values 0.24, 0.28 and 0.31 in the ratio 2–3:30–35:60–70, respectively. Probably the spots represented the endo/endo and exo/exo isomers in order of increasing $R_f$ values. (Found: C 27.14; H 2.94; I 48.5; N 5.40; O 15.18. Calc. for $C_{35}H_{44}I_6N_6O_{15}$: C 27.12; H 2.87; I 49.12; N 5.42; O 15.48).

The starting material 5-acetylamino-N,N'-bis(1,3-dihydroxy-2-propyl)-2,4,6-triiodoisophthalamide was prepared as follows:

5-Amino-N,N'-bis(1,3-dihydroxy-2-propyl)-2,4,6-triiodoisophthalamide (300 g) was suspended in acetic anhydride (1.5l) at 90° (on the oil bath) and then p-toluenesulphonic acid (3 g) was added. The mixture was heated for 4½ hours and then cooled slowly to room temperature. The product was collected on a filter and washed with small amounts of acetic anhydride. Yield: 353 g. The product was suspended in a mixture of methanol (600 ml) and water (300 ml) at room temperature and then pH was adjusted to about 11.5 by adding 5N sodium hydroxide (200 ml). This mixture was heated at 50° C. and more 5N sodium hydroxide (235 ml) was added dropwise in such a manner that pH was kept at about 10.5. After 2–3 hours pH did not decrease, and the hydrolysis was finished. After cooling to room temperature the mixture was acidified with 6N hydrochloric acid to pH 6.2. After stirring for two hours at room temperature, the mixture was cooled to 3° for 2–3 days. The product was collected on a filter, suspended in water (500 ml) and filtered again. Yield: 257 g. Melting point: above 270°. (Found: C 25.68; H 2.85; I 51.0; N 6.03. Calc. for $C_{16}H_{20}I_3N_3O_7$: C 25.72; H 2.70; I 50.96; N 5.62) TLC precoated TLC Plates Silica Gel 60 F-254 from Merck A. G. and developed in $CHCl_3$:MeOH=70:30) showed one spot with $R_f$ value 0.38.

EXAMPLE 3

1,3-Bis(acetylamino)-N,N'-bis[3,5-bis(2,3-dihydroxy-propylaminocarbonyl)-2,4,6-triiodophenyl]-2-hydroxy-propane. (Compound A)

5-Acetylamino-N,N'-bis(2,3-dihydroxypropyl)-2,4,6-triiodoisophthalamide (200 g, 0.268 mol) was slurried in water (800 ml) at room temperature. Sodium hydroxide (8.0 g, 0.20 mol) was added and epichlorohydrin (18.6 g, 0.20 mol) was added. After three days the starting material was dissolved and the solution neutralized with diluted hydrochloric acid. The solution was evaporated to dryness at 50° in vacuo finally purified by preparative LC in a similar manner as described in Example 1. Yield: 37 g. Melting point: 240°–250°. TLC (Precoated TLC Plates Silica Gel 60 F-254 from Merck A. G. and developed in n-BuOH:HOAc: $H_2O$=50:11:25) showed two spots with $R_f$ values 0.26 and 0.28 which probably represented the endo/exo and the exo/exo isomers, respectively. The ratio between the two spots was about 1:2 in order of increasing $R_f$ values. HPLC (the same conditions as described in example 1) showed two peaks with retention times 48.39 and 52.30 minutes, respectively. (Found: C 27.40; H 3.03; I 48.4; N 5.37; O 15.31. Calc. for $C_{35}H_{44}I_6O_{15}$: C 27.12; H 2.86; I 49.12; N 5.42; O 15.48)

EXAMPLE 4

1,4-Bis(acetylamino)-N,N'-bis[3,5-bis(1,3-dihydroxy-2-propylaminocarbonyl)-2,4,6-triiodophenyl]-2,3-dihydroxybutane. (Compound D)

5-Acetylamino-N,N'-bis(1,3-dihydroxy-2-propyl)-2,4,6-triiodoisophthalamide (224 g, 0.3 mol) was slurried in water (900 ml). Sodium hydroxide (6 ml 5M) was added and then 1,2,3,4,-diepoxybutane (19.4 g, 0.225 mol) was added. After three days TLC (Precoated TLC Plates Silica Gel 60 F-254 from Merck A. G. and developed in n-butanol: acetic acid: water=50:11:25) of the reaction solution showed three new spots with $R_f$ values 0.25, 0.26 and 0.29 representing the three endo/exo isomers of the desired product. The ratio of the spots were about 2–3: 30–35: 60–65 in order of increasing $R_f$ values. The reaction mixture was neutralized and then treated with strongly acid cation exchange resin (Amberlite TR L20) and strongly basic anion exchange resin (Dowex 1×4) to remove inorganic salts. After filtration the solution was evaported to dryness at 50° in vacuo. Yield: 240 g. The product was dissolved in methanol (1500 ml) and precipitated by adding isopropyl alcohol (1500 ml). Yield: 160 g. Further purification was performed by preparative LC in a similar manner as described in example 1. The eluent was 15% methanol in water. Yield: 101 g. Melting point: 310°–317° (Found: I 47.5 Calc. for $C_{36}H_{46}I_6O_{16}$: I 48.18).

Radiological compositions 1,4-Bis(acetylamino)-N,N'-bis[3,5-bis(2,3-dihydroxy-propylaminocarbonyl)-2,4,6-triiodophenyl]-2,3-dihydroxybutane (Compound C) of the present invention, trometamol (TRIS) and the edetate ($CaNa_2$ EDTA) are dissolved in water suitable for injection (approximately 500 ml). The pH is adjusted to 7.5 by means of hydrochloric acid (5M), and sodium chloride is added to make the solution isotonic. Water suitable for injection is added to make the volume of the solution up to 1000 ml.

The dispensed products are autoclaved for 20 min at 120° C.

| Example<br>Composition<br>1 liter | A<br>100 mg I/ml<br>Infusion | B<br>150 mg I/ml<br>Infusion | C<br>180 mg I/ml<br>Infusion | D<br>240 mg I/ml<br>Infusion | E<br>350 mg I/ml<br>Infusion | F<br>440 mg I/ml<br>Infusion |
|---|---|---|---|---|---|---|
| Compound C | 207.5 g | 311.5 g | 373.4 g | 497.9 g | 726.1 g | 912.9 g |
| Trometamol (TRIS) | 1.2 g | 1.2 g | 1.2 g | 1.2 g | 1.2 g | 1.2 g |
| Sodium/calcium edetate (CaNa$_2$EDTA) | 0.1 g | 0.1 g | 0.1 g | 0.1 g | 0.1 g | 0.1 g |
| Sodium chloride ad isotonic | | | | | | |
| Water for injection ad 1000 ml | | | | | | |
| HCl 5 M to make pH 7.5 | | | | | | |

The solution is membrane-filtered and dispensed into bottles or injection vials.

The infusion solutions are prepared in bottles of 250 ml and 500 ml, while solutions for injection are dispensed in 20, 50 and 100 ml injection vials.

We claim:
1. 1,3-bis(acetylamino)-N,N'-bis[3,5-bis(2,3-dihydroxypropylaminocarbonyl)-2,4,6-triiodophenyl]-2-hydroxypropane.

* * * * *